United States Patent
Manzer

(10) Patent No.: US 7,754,928 B2
(45) Date of Patent: Jul. 13, 2010

(54) METHOD OF MAKING 2-BUTANOL

(75) Inventor: Leo Ernest Manzer, Wilmington, DE (US)

(73) Assignee: E. I. duPont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/516,828

(22) PCT Filed: Nov. 30, 2007

(86) PCT No.: PCT/US2007/024677

§ 371 (c)(1), (2), (4) Date: May 29, 2009

(87) PCT Pub. No.: WO2008/069991

PCT Pub. Date: Jun. 12, 2008

(65) Prior Publication Data

US 2010/0056832 A1    Mar. 4, 2010

(51) Int. Cl.
*C07C 29/17* (2006.01)
*C07C 29/60* (2006.01)

(52) U.S. Cl. ...................................... 568/903

(58) Field of Classification Search .................. 568/903
See application file for complete search history.

(56) References Cited

U.S. PATENT DOCUMENTS

2005/0054736 A1    3/2005    Schlummer et al.

OTHER PUBLICATIONS

PCT/US 07/24677—International Search Report and Written Opinion, Mar. 25, 2008.
Manitto et al., Helvetica Chimica Acta, "Stereochemistry and fate of hydrogen atoms in the diol-dehydratase-catalyzed dehydration of meso-butane-2,3-diol," V 81, N11, pp. 2005-2016 (1998) ISSN:0018-019X.
Robert F. Nystrom et al., J. Am. Chem. Soc., "Reduction of Organic Compounds by Lithium Aluminum Hydride. I. Aldehydes, Ketones, Esters, Acid Chlorides and Acid Anhydrides" (1947) vol. 69, p. 1198.
Richard R. Emerson et al., Ind. Eng. Chem. Prod. Res. Dev., "Kinetics of Denydration of Aqueous 2,3 Butanediol in Methyl Ethyl Ketone" (1982) vol. 21, pp. 473-477.
Imre Bucsi et al., Tetrahedron, "Transformation of 1,2-Diokls over Perfluorinated Resinsulfonic Acids (Nafion-H)," vol. 50, No. 27, pp. 8195-8202 (1994).

*Primary Examiner*—Elvis O Price

(57) ABSTRACT

The present invention relates to a method for making 2-butanol from 2,3-butanediol by using a heterogeneous catalyst system that can function both as an acid catalyst and as a hydrogenation catalyst.

20 Claims, No Drawings

METHOD OF MAKING 2-BUTANOL

FIELD OF THE INVENTION

The present invention relates to a method for making 2-butanol from 2,3-butanediol.

BACKGROUND

Efforts directed at improving air quality and increasing energy production from renewable resources have resulted in renewed interest in alternative fuels, such as 2-butanol, that might replace gasoline and diesel fuel. Efforts are currently underway to increase the efficiency of 2-butanol production by fermentative microorganisms utilizing carbon sources from renewable feedstocks, such as corn waste and sugar cane bagasse, however these technologies have not yet been commercialized.

It is known that 2,3-butanediol ("BDO") can be converted to methylethylketone ("MEK") by heating BDO in the presence of a catalyst (Emerson, R. R., et al (Ind. Eng. Chem. Prod. Res. Dev. (1982) 21:473-477); Bucsi, I., et al (Tetrahedron (1994) 50:8195-8202). It has independently been shown that substantially pure MEK can be converted to 2-butanol by reacting MEK with hydrogen in the presence of a catalyst (Nystrom, R. F. and Brown, W. G. (J. Am. Chem. Soc. (1947) 69:1198). The present invention provides an improved process for producing 2-butanol directly from BDO using a heterogeneous catalyst system.

SUMMARY OF THE INVENTION

The present invention is a method of making 2-butanol comprising:

(a) contacting a reactant comprising dry or wet 2,3-butanediol, optionally in the presence of at least one inert solvent, with hydrogen in the presence of a heterogeneous catalyst system that can function both as an acid catalyst and as a hydrogenation catalyst at a temperature between about 75 and about 300 degrees Centigrade and a hydrogen pressure between about 345 kPa and about 20.7 MPa, to produce a reaction product comprising 2-butanol; and (b) recovering 2-butanol from the reaction product.

DETAILED DESCRIPTION OF THE INVENTION 2,3-Butanediol (BDO) may be obtained commercially, or by fermentation. The production of 2,3-butanediol by fermentation has been well-studied, particularly for its use as a precursor of 1,3-butadiene production during World War II, and has been reviewed in detail by Syu, M.-J. (Appl. Microbiol. Biotechnol (2001) 55:10-18). Strains of bacteria useful for producing BDO include *Klebsiella pneumoniae* and *Bacillus polymyxa*, as well as recombinant strains of *Escherichia coli*. Carbon and energy sources, culture media, and growth conditions (such as pH, temperature, aeration and inocululm) are dependent on the microbial strain used, and are described by Ledingham, G. A. and Neish, A. C. (Fermentative production of 2,3-butanediol, in Underkofler, L. A. and Hickey, R. J., Industrial Fermentations, Volume II, Chemical Publishing Co., Inc., New York, 1954, pages 27-93), Garg, S. K. and Jain, A. (Bioresource Technology (1995) 51:103-109), and Syu (supra). These references also describe the use of biomass as the carbon (i.e., sugar) source, as well as the bioreactors and additional fermentation equipment and conditions required for fermentation. One example wherein *K. pneumoniae* was utilized to produce BDO was provided by Grover, B. S., et al (World J. Microbiol. and Biotech. (1990) 6:328-332). Grover, B. S., et al described the production of BDO using *K. pneumoniae* NRRL B-199 grown on the reducing sugars in wood hydrolysate. Optimal conditions for a 48 hour fermentation were pH 6.0, a temperature of 30 degrees Centigrade, and 50 grams of reducing sugars per liter of medium.

BDO useful for the process of the invention can be either "dry BDO" or "wet BDO". "Dry BDO" refers to a material that is predominantly BDO, but may contain small amounts of water (under about 5% by weight relative to the weight of the BDO plus the water), and may contain small amounts of other materials from the fermentation broth as long as they do not materially affect the catalytic reaction previously described when performed with reagent grade BDO. In addition, the conversion of BDO to 2-butanol can be carried out in the presence of a substantial amount of water, i.e., "wet BDO". "Wet BDO" refers to a material having at least about 5% water relative to the weight of the BDO plus water combined. In a more specific embodiment, the wet BDO comprises from about 5% to about 80% water by weight relative to the weight of the water plus BDO.

BDO can be recovered from fermentation broth by a number of techniques, including vacuum membrane distillation using a microporous polytetrafluoroethylene membrane and solvent extraction using solvents such as ethyl acetate, diethyl ether, and n-butanol as reviewed by Syu (supra). In addition, Indian Patent No. IN 190544 describes treating fermentation broth comprising BDO with a mixture of barium hydroxide and zinc sulfate, followed by subjecting the treated fermentation broth to solvent extraction with an organic solvent to recover the BDO. Dry BDO can be obtained by distillation.

In the method of the present invention, both BDO and hydrogen are fed into a reactor containing a catalyst system that is capable of converting the BDO to 2-butanol. The reactor can be a fixed bed reactor, continuous stirred tank reactor (CSTR), pipe reactor, moving bed reactor, and other reactors that are known to those skilled in the art of catalysis, and the reaction may be conducted in the gas or liquid phase. The reactor temperature should be between about 75 and about 300 degrees Centigrade. In a more specific embodiment, the temperature of the reactor is from about 100 degrees Centigrade to about 260 degrees Centigrade. The feed materials may, if desired, be preheated before introduction into the reactor. The hydrogen pressure within the reactor should be between about 345 kPa and about 20.7 MPa. In a more specific embodiment, the pressure of the reactor is from about 690 kPa to about 3.45 MPa. The reaction may be conducted in the presence of at least one inert solvent. Suitable inert solvents include liquid hydrocarbons, liquid aromatic compounds, liquid ethers, 2-butanol, or combinations thereof. Preferred solvents include $C_5$ to $C_{20}$ straight-chain, branched or cyclic liquid hydrocarbons, $C_6$ to $C_{20}$ liquid aromatic compounds, and liquid dialkyl ethers wherein the individual alkyl groups of the dialkyl ether are straight-chain or branched, and wherein the total number of carbons of the dialkyl ether is from 4 to 16. More preferred liquid dialkyl ethers are those wherein the individual alkyl groups have from 2 to 5 carbons.

The heterogeneous catalyst system useful for the reaction is a catalyst system that can function both as an acid catalyst and as a hydrogenation catalyst. The heterogeneous catalyst system can comprise independent catalysts, i.e., at least one solid acid catalyst plus at least one solid hydrogenation catalyst. Alternatively, the heterogeneous catalyst system can comprise a dual function catalyst. For the purposes of this invention, a dual function catalyst is a catalyst wherein at least one solid acid catalyst and at least one solid hydrogenation catalyst are combined into one catalytic material.

Suitable acid catalysts for the present invention are heterogeneous (or solid) acid catalysts. The at least one solid acid catalyst may be supported on at least one catalyst support (herein referred to as a supported acid catalyst). Solid acid catalysts include, but are not limited to, (1) heterogeneous heteropolyacids (HPAs) and their salts, (2) natural clay minerals, such as those containing alumina or silica (including zeolites), (3) cation exchange resins, (4) metal oxides, (5) mixed metal oxides, (6) metal salts such as metal sulfides, metal sulfates, metal sulfonates, metal nitrates, metal phosphates, metal phosphonates, metal molybdates, metal tungstates, metal borates, and (7) combinations of groups 1 to 6. When present, the metal components of groups 4 to 6 may be selected from elements from Groups I, IIa, IIIa, VIIa, VIIIa, Ib and IIb of the Periodic Table of the Elements, as well as aluminum, chromium, tin, titanium and zirconium.

Suitable HPAs include compounds of the general Formula $X_a M_b O_c^{q-}$, where X is a heteroatom such as phosphorus, silicon, boron, aluminum, germanium, titanium, zirconium, cerium, cobalt or chromium, M is at least one transition metal such as tungsten, molybdenum, niobium, vanadium, or tantalum, and q, a, b, and c are individually selected whole numbers or fractions thereof. Nonlimiting examples of salts of HPAs are lithium, sodium, potassium, cesium, magnesium, barium, copper, gold and gallium, and onium salts such as ammonia. Methods for preparing HPAs are well known in the art and are described, for example, in Hutchings, G. and Vedrine, J., supra; selected HPAs are also available commercially, for example, through Sigma-Aldrich Corp. (St. Louis, Mo.). Examples of HPAs suitable for the process of the invention include tungstosilicic acid ($H_4[SiW_{12}O_{40}]^-xH_2O$), tungstophosphoric acid ($H_3[PW_{12}O_{40}]^-xH_2O$), molybdophosphoric acid ($H_3[PMo_{12}O_{40}]^-xH_2O$), molybdosilicic acid ($H_4[SiMo_{12}O_{40}]^-xH_2O$), vanadotungstosilicic acid ($H_{4+n}[SiV_nW_{12-n}O_{40}]^-xH_2O$), vanadotungstophosphoric acid ($H_{3+n}[PV_nW_{12-n}O_{40}]^-xH_2O$), vanadomolybdophosphoric acid ($H_{3+n}[PV_nMo_{12-n}O_{40}]^-xH_2O$), vanadomolybdosilicic acid ($H_{4+n}[SiV_nMo_{12-n}O_{40}]^-xH_2O$), molybdotungstosilicic acid ($H_4[SiMo_nW_{12-n}O_{40}]^-xH_2O$), molybdotungstophosphoric acid ($H_3[PMo_nW_{12-n}O_{40}]^-xH_2O$), wherein n in the Formulas is an integer of 1 to 11 and x is an integer of 1 or more.

Natural clay minerals are well known in the art and include, without limitation, kaolinite, bentonite, attapulgite, montmorillonite and zeolites.

Suitable cation exchange resins are styrene-divinylbenzene copolymer-based strong cation exchange resins such as Amberlyst® (Rohm & Haas; Philadelphia, Pa.), Dowex® (for example, Dowex® Monosphere M-31) (Dow; Midland, Mich.), CG resins from Resintech, Inc. (West Berlin, N.J.), and Lewatit resins such as MonoPlus™ S 100H from Sybron Chemicals Inc. (Birmingham, N.J.).

Fluorinated sulfonic acid polymers can also be used as solid acid catalysts for the process of the present invention. These acids are partially or totally fluorinated hydrocarbon polymers containing pendant sulfonic acid groups, which may be partially or totally converted to the salt form. One particularly suitable fluorinated sulfonic acid polymer is Nafion® perfluorinated sulfonic acid polymer, (E.I. du Pont de Nemours and Company, Wilmington, Del.). One preferred form is Nafion® Super Acid Catalyst, a bead-form strongly acidic resin which is a copolymer of tetrafluoroethylene and perfluoro-3,6-dioxa-4-methyl-7-octene sulfonyl fluoride, converted to either the proton ($H^+$), or the metal salt form.

Preferred solid acid catalysts include cation exchange resins, such as Amberlyst® 15 (Rohm and Haas, Philadelphia, Pa.), Amberlite® 120 (Rohm and Haas), Nafion®, and natural clay materials, including zeolites such as mordenite.

When used, the at least one support for the at least one solid acid catalyst can be any solid substance that is inert under the reaction conditions including, but not limited to, oxides such as silica, alumina and titania, compounds thereof or combinations thereof; barium sulfate; calcium carbonate; zirconia; carbons, particularly acid washed carbon; and combinations thereof. Acid washed carbon is a carbon that has been washed with an acid, such as nitric acid, sulfuric acid or acetic acid, to remove impurities. The support can be in the form of powder, granules, pellets, or the like. The supported acid catalyst can be prepared by depositing the acid catalyst on the support by any number of methods well known to those skilled in the art of catalysis, such as spraying, soaking or physical mixing, followed by drying, calcination, and if necessary, activation through methods such as reduction or oxidation. The preferred loading of the at least one acid catalyst on the at least one support is from about 0.1 weight percent to about 20 weight percent based on the combined weights of the at least one acid catalyst plus the at least one support.

Examples of supported acid catalysts include, but are not limited to, phosphoric acid on silica, Nafion® on silica, HPAs on silica, sulfated zirconia and sulfated titania.

The heterogeneous catalyst system useful for the invention must also comprise at least one solid hydrogenation catalyst. The at least one solid hydrogenation catalyst may be supported on at least one catalyst support (herein referred to as a supported hydrogenation catalyst).

The hydrogenation catalyst may be a metal selected from the group consisting of nickel, copper, chromium, cobalt, rhodium, ruthenium, rhenium, osmium, iridium, platinum, palladium, platinum black; compounds thereof; and combinations thereof. It is well-known that Raney-type catalysts may be formed from some of the metals listed above (for example, Raney Nickel® (W.R. Grace & Co., Columbia, Md.)), and these Raney-type catalysts are also expected to be useful as hydrogenation catalysts for the present invention. A promoter such as, without limitation, tin, zinc, copper, gold, silver and combinations thereof may be used to affect the reaction, for example, by increasing activity and catalyst lifetime.

Preferred hydrogenation catalysts include ruthenium, iridium, palladium; compounds thereof; and combinations thereof.

The at least one support for the at least one solid hydrogenation catalyst can be any solid substance that is inert under the reaction conditions including, but not limited to, oxides such as silica, alumina and titania; barium sulfate; calcium carbonate; zirconia; carbons, particularly acid washed carbon; and combinations thereof. The catalyst support can be in the form of powder, granules, pellets, or the like. The supported hydrogenation catalyst can be prepared by depositing the hydrogenation catalyst on the support by any number of methods well known to those skilled in the art of catalysis, such as spraying, soaking or physical mixing, followed by drying, calcination, and if necessary, activation through methods such as reduction. The preferred loading of the metal of the at least one solid hydrogenation catalyst on the at least one support is from about 0.1 weight percent to about 20 weight percent based on the combined weights of the metal of the at least one hydrogenation catalyst plus the at least one support.

Preferred supported hydrogenation catalysts include, but are not limited to, ruthenium on carbon, ruthenium on alumina, and iridium on carbon.

Examples of heterogeneous catalyst systems include any unsupported or supported solid acid catalyst as described above with any unsupported or supported hydrogenation catalyst as described above. In a more specific embodiment, the heterogeneous catalyst system can include an unsupported or supported solid acid catalyst wherein the solid acid catalyst is selected from the group consisting of (1) heterogeneous heteropolyacids (HPAs) and their salts, (2) natural clay minerals, such as those containing alumina or silica (including zeolites), (3) cation exchange resins, (4) metal oxides, (5) mixed metal oxides, (6) metal salts such as metal sulfides, metal sulfates, metal sulfonates, metal nitrates, metal phosphates, metal phosphonates, metal molybdates, metal tungstates, metal borates, and (7) combinations of groups 1 to 6, and an unsupported or supported hydrogenation catalyst wherein the hydrogenation catalyst is selected from metals from the group consisting of nickel, copper, chromium, cobalt, rhodium, ruthenium, rhenium, osmium, iridium, platinum, palladium, platinum black; compounds thereof; and combinations thereof, wherein the catalyst support for either the solid acid catalyst and/or the hydrogenation catalyst can be selected from the group consisting of oxides such as silica, alumina and titania; barium sulfate; calcium carbonate; zirconia; carbons, particularly acid washed carbon; and combinations thereof.

In an even more specific embodiment, the heterogeneous catalyst system can include an unsupported or supported solid acid catalyst wherein the solid acid catalyst is selected from the group consisting of cation exchange resins and natural clay minerals, and an unsupported or supported hydrogenation catalyst wherein the hydrogenation catalyst is selected from metals from the group consisting of nickel, copper, chromium, cobalt, rhodium, ruthenium, rhenium, osmium, iridium, platinum, palladium, platinum black, compounds thereof and combinations thereof.

In an even more specific embodiment, the heterogeneous catalyst system can include an unsupported or supported solid acid catalyst wherein the solid acid catalyst is selected from the group consisting of cation exchange resins and natural clay minerals, and an unsupported or supported hydrogenation catalyst wherein the hydrogenation catalyst is selected from metals from the group consisting of ruthenium, iridium, palladium, compounds thereof, and combinations thereof.

The heterogeneous catalyst system can also be a dual function catalyst. Dual function catalysts (also known as bifunctional catalysts) have been reported; for example, Sie, S. T. has described improved catalyst stability using a dual function catalyst to carry out isomerization reactions (Ertl, G., et al (ed) in Handbook of Heterogeneous Catalysis, Volume 4, Section 3.12.4.2 (1997) VCH Verlagsgesellschaft mbH, Weinheim, Germany). In the present invention, the dual function catalyst can be a hydrogenation catalyst on an acidic catalyst support. Such dual function catalysts can be prepared in such a way that the catalyst support retains acid functionality after deposition of the hydrogenation catalyst. The dual function catalyst can be prepared by depositing the metal of the hydrogenation catalyst on the acidic catalyst support by any number of methods well known to those skilled in the art of catalysis, such as spraying, soaking or physical mixing, followed by drying, calcination, and if necessary, activation through methods such as reduction. For example, U.S. Pat. No. 6,448,198 (Column 4, line 55 through Column 18, line 9) describes a solid catalyst containing sulfated zirconia and at least one hydrogenating transition metal for use in hydrocarbon transformation reactions (such as isomerization and alkylation), as well as methods for preparing such catalysts. According to one method, the catalyst can be prepared by depositing hydrated zirconia on a catalytic support, calcining the solid, sulfating the solid, depositing a hydrogenating transition metal on the solid, and performing a final calcination of the solid.

A suitable dual function catalyst can be, but is not limited to, a hydrogenation catalyst comprising a metal selected from the group consisting of nickel, copper, chromium, cobalt, rhodium, ruthenium, rhenium, osmium, iridium, platinum, and palladium; compounds thereof; and combinations thereof deposited by any means described above on an acid catalyst selected from the group consisting of (1) heterogeneous heteropolyacids (HPAs) and their salts, (2) natural clay minerals, such as those containing alumina or silica (including zeolites), (3) cation exchange resins, (4) metal oxides, (5) mixed metal oxides, (6) metal salts such as metal sulfides, metal sulfates, metal sulfonates, metal nitrates, metal phosphates, metal phosphonates, metal molybdates, metal tungstates, metal borates, and (7) combinations of groups 1 to 6.

Preferred dual function catalysts comprise a hydrogenation catalyst comprising a metal selected from the group consisting of nickel, copper, chromium, cobalt, rhodium, ruthenium, rhenium, osmium, iridium, platinum, and palladium; compounds thereof; and combinations thereof deposited by any means described above on an acid catalyst selected from the group consisting of (1) natural clay minerals, such as those containing alumina or silica (including zeolites), (2) cation exchange resins, (3) metal salts such as metal sulfides, metal sulfates, metal sulfonates, metal nitrates, metal phosphates, metal phosphonates, metal molybdates, metal tungstates, metal borates, and (4) combinations of groups 1 to 3.

In addition, dual function catalysts may comprise at least one hydrogenation catalyst on at least one supported acid catalyst. Examples include, but are not limited to, a hydrogenation catalyst comprising a metal selected from the group consisting of nickel, copper, chromium, cobalt, rhodium, ruthenium, rhenium, osmium, iridium, platinum, and palladium; compounds thereof; and combinations thereof deposited by any means described above on sulfated titania, sulfated zirconia, phosphoric acid on silica, and Nafion® on silica. In a more specific embodiment, platinum can be deposited by any means described above on sulfated titania, sulfated zirconia, phosphoric acid on silica, HPAs on silica, or Nafion® on silica.

The reaction product comprises 2-butanol, as well as water, and may comprise unreacted BDO and/or methylethylketone (MEK). 2-Butanol can be recovered by a refining process that includes at least one distillation step (Doherty, M. F. and M. F. Malone, *Conceptual Design of Distillation Systems*, McGraw-Hill, New York, 2001). When the present process is carried out using dry BDO, it is expected that there will be too little water to form azeotropic mixtures with either MEK or 2-butanol that are present in the reaction product. In such a system, n components can be separated by n−1 distillation columns as is well known to those skilled in the art, taking into account the boiling points of the various components to be separated.

When the present process is carried out using wet BDO, it is expected that the reaction product will contain a sufficiently high water content that azeotropic mixtures of MEK and 2-butanol will be present. In such a situation, a more complex distillation scheme involving extractive distillation will be required. Extractive distillation requires the use of an entrainer. A successful entrainer must form one or more binary and/or ternary azeotropes with water and possibly 2-butanol that has a boiling point lower than the 2-butanol-water azeotrope. This way the entrainer-containing azeotrope(s) will distill overhead. The boiling point of the entrainer is not required to be below that of the 2-butanol-water azeotrope, only its azeotropes must be. The azeotropes formed by the entrainer should also be heterogeneous so that decantation can be used to cross the azeotropes and distillation boundaries. It is preferable that the entrainer has very low solubility with water. Additionally, the composition of the feed to the azeotropic distillation column can affect the feasibility and/or design of the process. Toluene can be used as the entrainer to effect the distillative separation of 2-butanol from water. Similarly, ethylene glycol can be used as the entrainer to effect the distillative separation of MEK from water.

Unreacted BDO and MEK can be returned to the reaction for conversion to 2-butanol.

EXAMPLES

In the following examples, "C" is degrees Centigrade, "mg" is milligram; "gm" is gram, "ml" is milliliter; "temp" is temperature; "MPa" is mega Pascal; "GC/MS" is gas chromatography/mass spectrometry; "SCCM" is standard cubic centimeters per minute; "AWC" is acid washed carbon; "conv." is conversion; "sel." is selectivity.

Amberlyst® and Amberlite® (manufactured by Rohm and Haas, Philadelphia, Pa.), tungstic acid, phosphotungstic acid on $SiO_2$ were obtained from Alfa Aesar (Ward Hill, Mass.); CBV-3020E was obtained from PQ Corporation (Berwyn, Pa.); Nafion®/$SiO_2$ and ESCAT catalysts can be obtained from Engelhard (Iselin, N.J.); ruthenium on alumina was obtained from Aldrich (St. Louis, Mo.) or from Engelhard; ruthenium on carbon was obtained from Englehard where indicated in the tables below, or from Strem Chemicals, Inc. (Newburyport, Mass.); Deloxan® was Deloxan (r), Type ASP1/7, Batch Number T304, particle size 0.4 to 1.25 mm (obtained from Degussa (Parsippany, N.J.)); and H-Mordenite can be obtained from Zeolyst Intl. (Valley Forge, Pa.). 2,3-Butanediol was obtained from Aldrich, St. Louis, Mo.

Catalyst Preparation: 5% Pt on Acid Washed Carbon (Obtained from Calsicat)

In a 150 ml beaker, a solution was made up of 4.5 ml 0.3 M $H_2PtCl_6$ with 4.0 ml deionized $H_2O$. To the beaker were added 4.75 g Calsicat (Engelhard Corp.) Acid Washed Carbon (12×20 mesh, dried at 120° C. overnight). The slurry was allowed to stand at room temperature for 1 hr with occasional stirring, followed by drying at 120° C. overnight with frequent stirring (until free flowing).

In an alumina boat, in a quartz lined tube furnace, the catalyst was purged with 500 SCCM $N_2$ at room temperature for 15 min and then with 100 SCCM He at room temperature for 15 min. The catalyst was heated to 150° C. and held at 150° C. under He for 1 hr. At this point, 100 SCCM $H_2$ were added and the sample was held at 150° C. under He and $H_2$ for 1·hr. The temperature was increased to 300° C. and the catalyst was reduced at 300° C. under He—$H_2$ for 8 hrs. The $H_2$ was stopped, the sample was held at 300° C. under He for 30 min and then cooled to room temperature in flowing He. The catalyst was finally passivated in 1.5% $O_2$ in $N_2$ at 500 SCCM for 1 hr at room temperature and weighed 4.93 g when unloaded.

Additional catalysts used in the present invention were prepared following a similar procedure.

General Procedure

In the following experiments, BDO (obtained from Aldrich), a hydrogenation catalyst and a solid acid catalyst were combined in a 5 ml pressurized reactor. The reactor was then charged with hydrogen and heated to reactor temperature for a period of time. The pressure, temperature and time are listed in the examples below. Unless otherwise indicated, 1 gm of BDO was combined with 0.05 gm of a hydrogenation catalyst and 0.1 gm of a solid acid catalyst. At the end of the reaction the vessel was cooled, vented and the products analyzed by GC/MS using a capillary column (either (a) CP-Wax 58 [Varian; Palo Alto, Calif.], 25 m×0.25 mm, 45 C/6 min, 10 C/min up to 200 C, 200 C/10 min, or (b) DB-1701 [J&W (available through Agilent; Palo Alto, Calif.)], 30 m×0.25 mm, 50 C/10 min, 10 C/min up to 250 C, 250 C/2 min).

The examples below were performed according to this procedure under the conditions indicated for each example. "Selectivity" refers to the percent of a particular reaction product (not including the unreacted reactants). "Conversion" refers to the percent of a particular reactant that is converted to product.

Examples 1-5

BDO was combined with the indicated hydrogenation catalyst and Amberlyst®15 at a hydrogen pressure of 6.21 MPa. The reaction was run at 150° C. for 2 hours.

| Ex. No. | Hydrogenation Catalyst | Acid Catalyst | BDO Conv. (%) | 2-BuOH Sel. (%) |
|---|---|---|---|---|
| 1 | 5% Pt/AWC | Amberlyst ®15 | 68.0 | 1.6 |
| 2 | 5% Ru/AWC | Amberlyst ®15 | 34.6 | 43.6 |
| 3 | 5% Pd/AWC | Amberlyst ®15 | 70.9 | 1.6 |
| 4 | 5% Re/AWC | Amberlyst ®15 | 74.0 | 3.1 |
| 5 | 5% Ir/AWC | Amberlyst ®15 | 48.2 | 19.0 |

Examples 6-12

The conversion of BDO was determined in the presence of increasing concentrations of hydrogenation catalyst. ESCAT 440 (5% Ru/C) was combined with Amberlite®IR120 at a hydrogen pressure of 5.52 MPa. The reaction was run at 150° C. for 2 hours.

| Ex. No. | Hydrogenation Catalyst | Hydrogenation Catalyst (mg) | Acid Catalyst | BDO Conv. (%) | 2-BuOH Sel. (%) |
|---|---|---|---|---|---|
| 6 | ESCAT 440 (CP97) | 0.0245 | Amberlite ® IR 120 | 50.9 | 28.9 |
| 7 | ESCAT 440 (CP97) | 0.0497 | Amberlite ® IR 120 | 48.4 | 30.4 |
| 8 | ESCAT 440 (CP97) | 0.0748 | Amberlite ® IR 120 | 41.8 | 32.1 |

-continued

| Ex. No. | Hydrogenation Catalyst | Hydrogenation Catalyst (mg) | Acid Catalyst | BDO Conv. (%) | 2-BuOH Sel. (%) |
|---|---|---|---|---|---|
| 9 | ESCAT 440 (CP97) | 0.1026 | Amberlite ® IR 120 | 41.3 | 23.6 |
| 10 | ESCAT 440 (CP97) | 0.1255 | Amberlite ® IR 120 | 38.7 | 24.4 |
| 11 | ESCAT 440 (CP97) | 0.1504 | Amberlite ® IR 120 | 34.4 | 22.8 |
| 12 | ESCAT 440 (CP97) | 0.1744 | Amberlite ® IR 120 | 27.8 | 22.8 |

Examples 13-19

BDO was combined with the indicated hydrogenation catalyst and Amberlite®IR 120 at a hydrogen pressure of 5.52 MPa. The reaction was run at 150° C. for 2 hours. The hydrogenation catalyst comprised ruthenium on various supports.

| Ex. No. | Hydrogenation Catalyst | Acid Catalyst | BDO Conv. (%) | 2-BuOH Sel. (%) |
|---|---|---|---|---|
| 13 | 5% Ru/C (ESCAT 440) | Amberlite ® IR 120 | 43.8 | 36.0 |
| 14 | 5% Ru/C (ESCAT 440 (CP97)) | Amberlite ® IR 120 | 46.6 | 31.3 |
| 15 | 5% Ru/Al$_2$O$_3$ (AP38) | Amberlite ® IR 120 | 44.7 | 37.5 |
| 16 | 5% Ru/Al$_2$O$_3$ Aldrich | Amberlite ® IR 120 | 49.0 | 38.1 |
| 17 | 5% Ru/C (Strem) | Amberlite ® IR 120 | 54.2 | 17.2 |
| 18 | 5% Ru/Al$_2$O$_3$ (ESCAT 44) | Amberlite ® IR 120 | 44.2 | 36.3 |
| 19 | 5% Ru/AWC | Amberlite ® IR 120 | 40.7 | 50.4 |

Examples 20-26

BDO was combined with the indicated hydrogenation catalyst and Amberlyst®15 (Wet) at a hydrogen pressure of 5.52 MPa. The reaction was run at 150° C. for 2 hours.

| Ex. No. | Hydrogenation Catalyst | Acid Catalyst | BDO Conv. (%) | 2-BuOH Sel. (%) |
|---|---|---|---|---|
| 20 | 5% Ru/C (ESCAT 440) | Amberlyst ®15 (Wet) | 82.4 | 15.7 |
| 21 | 5% Ru/C (ESCAT 440 (CP97)) | Amberlyst ®15 (Wet) | 70.4 | 17.8 |
| 22 | 5% Ru/Al$_2$O$_3$ (AP38) | Amberlyst ®15 (Wet) | 56.3 | 12.8 |
| 23 | 5% Ru/Al$_2$O$_3$ Aldrich | Amberlyst ®15 (Wet) | 63.9 | 14.2 |
| 24 | 5% Ru/C (Strem) | Amberlyst ®15 (Wet) | 63.8 | 14.2 |
| 25 | 5% Ru/Al$_2$O$_3$ (ESCAT 44) | Amberlyst ®15 (Wet) | 58.9 | 10.4 |
| 26 | 5% Ru/AWC | Amberlyst ®15 (Wet) | 54.4 | 22.5 |

Examples 27-31

BDO was combined with the indicated hydrogenation catalyst and Amberlite®IR 120 at a hydrogen pressure of 5.52 MPa. The reaction was run at 150° C. for 2 hours.

| Ex. No. | Hydrogenation Catalyst | Acid Catalyst | BDO Conv. (%) | 2-BuOH Sel. (%) |
|---|---|---|---|---|
| 27 | 5% Pt/AWC | Amberlite ® IR 120 | 62.9 | 1.8 |
| 28 | 5% Ru/AWC | Amberlite ® IR 120 | 44.3 | 50.9 |
| 29 | 5% Pd/AWC | Amberlite ® IR 120 | 57.1 | 2.1 |
| 30 | 5% Re/AWC | Amberlite ® IR 120 | 58.8 | 1.7 |
| 31 | 5% Ir/AWC | Amberlite ® IR 120 | 55.9 | 17.6 |

Examples 32-38

BDO was combined with ruthenium on acid-washed carbon as the hydrogenation catalyst and various acid catalysts at a hydrogen pressure of 5.52 MPa. The reaction was run at 150° C. for 2 hours.

| Ex. No. | Hydrogenation Catalyst | Acid Catalyst | BDO Conv. (%) | 2-BuOH Sel. (%) |
|---|---|---|---|---|
| 32 | 5% Ru/AWC | Amberlyst ®15 (Wet) | 58.3 | 19.3 |
| 33 | 5% Ru/AWC | Amberlite ® IR 120 | 43.6 | 51.7 |
| 34 | 5% Ru/AWC | Amberlite ® IRC-50 | 7.3 | 8.1 |
| 35 | 5% Ru/AWC | 13% Nafion ®/SiO$_2$ | 27.7 | 7.7 |
| 36 | 5% Ru/AWC | Tungstic Acid (99%) | 17.3 | 7.2 |
| 37 | 5% Ru/AWC | 4% Phosphotungstic Acid/SiO$_2$ | 27.6 | 18.5 |
| 38 | 5% Ru/AWC | H-Mordenite | 26.0 | 27.0 |

Examples 39-45

BDO was combined with ruthenium on acid-washed carbon as the hydrogenation catalyst and various acid catalysts at a hydrogen pressure of 5.52 MPa. The reaction was run at 125° C. for 2 hours.

| Ex. No. | Hydrogenation Catalyst | Acid Catalyst | BDO Conv. (%) | 2-BuOH Sel. (%) |
|---|---|---|---|---|
| 39 | 5% Ru/AWC | Amberlyst ®15 (Wet) | 68.9 | 4.3 |
| 40 | 5% Ru/AWC | Amberlite ® IR 120 | 56.8 | 15.7 |
| 41 | 5% Ru/AWC | Amberlite ® IRC-50 | 7.2 | 7.4 |
| 42 | 5% Ru/AWC | 13% Nafion ®/SiO$_2$ | 21.7 | 30.6 |
| 43 | 5% Ru/AWC | Tungstic Acid (99%) | 16.2 | 6.7 |
| 44 | 5% Ru/AWC | 4% Phosphotungstic Acid/SiO$_2$ | 18.9 | 25.2 |
| 45 | 5% Ru/AWC | H-Mordenite | 22.7 | 22.5 |

Examples 46-52

BDO was combined with ruthenium on acid-washed carbon as the hydrogenation catalyst and various acid catalysts at a hydrogen pressure of 7.58 MPa. The reaction was run at 150° C. for 2 hours.

| Ex. No. | Hydrogenation Catalyst | Acid Catalyst | BDO Conv. (%) | 2-BuOH Sel. (%) |
|---|---|---|---|---|
| 46 | 5% Ru/AWC | Amberlyst ®15 (Wet) | 51.4 | 31.2 |
| 47 | 5% Ru/AWC | Amberlite ® IR 120 | 44.6 | 51.2 |
| 48 | 5% Ru/AWC | Amberlite ® IRC-50 | 15.4 | 4.5 |
| 49 | 5% Ru/AWC | 13% Nafion ®/SiO$_2$ | 23.1 | 25.6 |
| 50 | 5% Ru/AWC | Tungstic Acid (99%) | 14.6 | 6.9 |
| 51 | 5% Ru/AWC | 4% Phosphotungstic Acid/SiO$_2$ | 17.1 | 15.3 |
| 52 | 5% Ru/AWC | H-Mordenite | 19.3 | 29.2 |

Examples 53-57

BDO was combined with the indicated hydrogenation catalyst and Amberlyst®15 (Wet) at a hydrogen pressure of 7.45 MPa. The reaction was run at 200° C. for 1 hour.

| Ex. No. | Hydrogenation Catalyst | Acid Catalyst | BDO Conv. (%) | 2-BuOH Sel. (%) |
|---|---|---|---|---|
| 53 | 5% Pt/AWC | Amberlyst ®15 (Wet) | 100.0 | 0.9 |
| 54 | 5% Ru/AWC | Amberlyst ®15 (Wet) | 99.9 | 1.4 |
| 55 | 5% Pd/AWC | Amberlyst ®15 (Wet) | 99.9 | 0.1 |
| 56 | 5% Re/AWC | Amberlyst ®15 (Wet) | 99.8 | 5.7 |
| 57 | 5% Ir/AWC | Amberlyst ®15 (Wet) | 98.6 | 3.8 |

Examples 58-61

BDO was combined with ruthenium on acid-washed carbon as the hydrogenation catalyst and various acid catalysts at a hydrogen pressure of 6.55 MPa. The reaction was run at 150° C. for 2 hours.

| Ex. No. | Hydrogenation Catalyst | Acid Catalyst | BDO Conv. (%) | 2-BuOH Set. (%) |
|---|---|---|---|---|
| 58 | 5% Ru/AWC | Amberlyst ®15 | 36.6 | 42.6 |
| 59 | 5% Ru/AWC | 13% Nafion ®/SiO$_2$ | 26.8 | 27.8 |
| 60 | 5% Ru/AWC | Deloxan ® | 19.0 | 33.1 |
| 61 | 5% Ru/AWC | H-Mordenite | 24.5 | 23.7 |

Examples 58-63

BDO was combined with rhenium on acid-washed carbon as the hydrogenation catalyst and various acid catalysts at a hydrogen pressure of 6.76 MPa. The reaction was run at 150° C. for 2 hours.

| Ex. No. | Hydrogenation Catalyst | Acid Catalyst | BDO Conv. (%) | 2-BuOH Sel. (%) |
|---|---|---|---|---|
| 58 | 5% Re/AWC | Amberlyst ®15 (Wet) | 78.3 | 5.7 |
| 59 | 5% Re/AWC | 13% Nafion ®/SiO$_2$ | 48.2 | 0.3 |
| 60 | 5% Re/AWC | Deloxan ® | 21.1 | 0.8 |
| 61 | 5% Re/AWC | H-Mordenite | 33.2 | 0.8 |
| 62 | 5% Re/AWC | Amberlite ® IR 120 | 56.2 | 1.8 |
| 63 | 5% Re/AWC | Amberlyst ®36 (Wet) | 64.1 | 4.5 |

Examples 64-70

BDO was combined with iridium on acid-washed carbon as the hydrogenation catalyst and various acid catalysts at a hydrogen pressure of 6.76 MPa. The reaction was run at 150° C. for 2 hours.

| Ex. No. | Hydrogenation Catalyst | Acid Catalyst | BDO Conv. (%) | 2-BuOH Sel. (%) |
|---|---|---|---|---|
| 64 | 5% Ir/AWC | Amberlyst ®15 (Wet) | 48.6 | 19.3 |
| 65 | 5% Ir/AWC | 13% Nafion ®/SiO$_2$ | 26.8 | 14.2 |
| 66 | 5% Ir/AWC | Deloxan ® | 17.2 | 24.4 |
| 67 | 5% Ir/AWC | H-Mordenite | 20.2 | 20.8 |
| 68 | 5% Ir/AWC | Amberlite ® IR 120 | 46.2 | 37.3 |
| 69 | 5% Ir/AWC | Amberlyst ®36 (Wet) | 41.3 | 32.4 |
| 70 | 5% Ir/AWC | Tungstic Acid (99%) | 25.5 | 6.1 |

Examples 71-75

BDO was combined with the indicated hydrogenation and acid catalysts at a hydrogen pressure of 6.21 MPa. The reaction was run at 150° C. for 2 hours. The hydrogenation catalyst comprised ruthenium on various supports.

| Ex. No. | Hydrogenation Catalyst | Acid Catalyst | BDO Conv. (%) | 2-BuOH Sel. (%) |
|---|---|---|---|---|
| 71 | 5% Ru/C (ESCAT 440) | Amberlyst ®15 | 40.6 | 22.5 |
| 72 | 5% Ru/Al$_2$O$_3$ (AP38) | Deloxan ® | 92.2 | 1.5 |
| 73 | 5% Ru/C (Strem) | Amberlite ® IR 120 | 37.3 | 28.4 |
| 74 | 5% Ru/Al$_2$O$_3$ (ESCAT 44) | Amberlyst ®36 (Wet) | 48.2 | 17.0 |
| 75 | 5% Ru/AWC | Amberlite ® IRC-50 | 7.1 | 11.9 |

Examples 76-81

BDO was combined with the indicated hydrogenation and acid catalysts at a hydrogen pressure of 4.48 MPa. The reaction was run at 150° C. for 2 hours. The hydrogenation catalyst comprised ruthenium on various supports.

| Ex. No. | Hydrogenation Catalyst | Acid Catalyst | BDO Conv. (%) | 2-BuOH Sel. (%) |
|---|---|---|---|---|
| 76 | 5% Ru/C (ESCAT 440) | Amberlyst ®15 (Wet) | 53.1 | 11.0 |
| 77 | 5% Ru/Al$_2$O$_3$ (AP38) | Deloxan ® | 21.6 | 5.4 |
| 78 | 5% Ru/Al$_2$O$_3$ (Aldrich) | H-Mordenite | 16.9 | 14.1 |

-continued

| Ex. No. | Hydrogenation Catalyst | Acid Catalyst | BDO Conv. (%) | 2-BuOH Sel. (%) |
|---|---|---|---|---|
| 79 | 5% Ru/C (Strem) | Amberlite ® IR 120 | 50.7 | 20.7 |
| 80 | 5% Ru/Al$_2$O$_3$ (ESCAT 44) | Amberlyst ®36 (Wet) | 68.8 | 8.6 |
| 81 | 5% Ru/AWC | Amberlite ® IRC-50 | 6.1 | 15.5 |

Examples 82-87

BDO was combined with the indicated hydrogenation and acid catalysts at a hydrogen pressure of 3.17 MPa. The reaction was run at 150° C. for 2 hours. The hydrogenation catalyst comprised ruthenium on various supports.

| Ex. No. | Hydrogenation Catalyst | Acid Catalyst | BDO Conv. (%) | 2-BuOH Sel. (%) |
|---|---|---|---|---|
| 82 | 5% Ru/C (ESCAT 440) | Amberlyst ®15 (Wet) | 51.5 | 6.6 |
| 83 | 5% Ru/Al$_2$O$_3$ (AP38) | Deloxan ® | 11.6 | 9.1 |
| 84 | 5% Ru/Al$_2$O$_3$ (Aldrich) | H-Mordenite | 24.2 | 11.7 |
| 85 | 5% Ru/C (Strem) | Amberlite ® IR 120 | 56.1 | 7.7 |
| 86 | 5% Ru/Al$_2$O$_3$ (ESCAT 44) | Amberlyst ®36 (Wet) | 56.9 | 4.5 |
| 87 | 5% Ru/AWC | Amberlite ® IRC-50 | 12.2 | 8.4 |

Examples 88-94

BDO was combined with ruthenium on acid-washed carbon as the hydrogenation catalyst and various acid catalysts at a hydrogen pressure of 1.38 MPa. The reaction was run at 150° C. for 2 hours.

| Ex. No. | Hydrogenation Catalyst | Acid Catalyst | BDO Conv. (%) | 2-BuOH Sel. (%) |
|---|---|---|---|---|
| 88 | 5% Ru/AWC | Amberlyst ®15 (Wet) | 76.9 | 0.7 |
| 89 | 5% Ru/AWC | Amberlite ® IR 120 | 21.9 | 21.1 |
| 90 | 5% Ru/AWC | Amberlite ® IRC-50 | 8.5 | 6.0 |
| 91 | 5% Ru/AWC | 13% Nafion ®/SiO$_2$ | 52.5 | 5.1 |
| 92 | 5% Ru/AWC | Tungstic Acid (99%) | 19.5 | 5.6 |
| 93 | 5% Ru/AWC | 4% Phosphotungstic Acid/SiO$_2$ | 25.0 | 16.9 |
| 94 | 5% Ru/AWC | H-Mordenite | 25.2 | 16.4 |

Examples 95-101

BDO was combined with ruthenium on acid-washed carbon as the hydrogenation catalyst and various acid catalysts at a hydrogen pressure of 3.45 MPa. The reaction was run at 150° C. for 2 hours.

| Ex. No. | Hydrogenation Catalyst | Acid Catalyst | BDO Conv. (%) | 2-BuOH Sel. (%) |
|---|---|---|---|---|
| 95 | 5% Ru/AWC | Amberlyst ®15 (Wet) | 88.5 | 2.9 |
| 96 | 5% Ru/AWC | Amberlite ® IR 120 | 53.8 | 15.7 |
| 97 | 5% Ru/AWC | Amberlite ® IRC-50 | 10.4 | 6.1 |
| 98 | 5% Ru/AWC | 13% Nafion ®/SiO$_2$ | 22.7 | 22.0 |
| 99 | 5% Ru/AWC | Tungstic Acid (99%) | 15.0 | 7.9 |
| 100 | 5% Ru/AWC | 4% Phosphotungstic Acid/SiO$_2$ | 26.9 | 13.5 |
| 101 | 5% Ru/AWC | H-Mordenite | 21.7 | 20.1 |

Examples 102-106

BDO was combined with the indicated hydrogenation catalyst and Amberlyst®15 at a hydrogen pressure of 6.55 MPa in the presence of 50 weight percent water (relative to the total weight of the BDO plus water). The reaction was run at 150° C. for 2 hours.

| Ex. No. | Hydrogenation Catalyst | Acid Catalyst | Solvent | BDO Conv. (%) | 2-BuOH Sel. (%) |
|---|---|---|---|---|---|
| 102 | 5% Pt/AWC | Amberlyst ®15 | H$_2$O | 28.0 | 5.5 |
| 103 | 5% Ru/AWC | Amberlyst ®15 | H$_2$O | 20.1 | 38.2 |
| 104 | 5% Pd/AWC | Amberlyst ®15 | H$_2$O | 21.0 | 29.8 |
| 105 | 5% Re/AWC | Amberlyst ®15 | H$_2$O | 33.3 | 4.4 |
| 106 | 5% Ir/AWC | Amberlyst ®15 | H$_2$O | 19.3 | 34.4 |

Examples 107-113

BDO was combined with platinum on acid-washed carbon as the hydrogenation catalyst and various acid catalysts at a hydrogen pressure of 6.76 MPa in the presence of 50 weight percent trimethylpentane (relative to the total weight of the BDO plus trimethylpentane). The reaction was run at 150° C. for 2 hours.

| Ex. No. | Hydrogenation Catalyst | Acid Catalyst | Solvent | BDO Conv. (%) | 2-BuOH Sel. (%) |
|---|---|---|---|---|---|
| 107 | 5% Pt/AWC | Amberlite ® IRC-50 | TMP | 6.2 | 7.4 |
| 108 | 5% Pt/AWC | Amberlyst ®15 | TMP | 100.0 | 0.8 |
| 109 | 5% Pt/AWC | 13% Nafion ®/SiO$_2$ | TMP | 16.3 | 7.1 |
| 110 | 5% Pt/AWC | CBV 3020 | TMP | 24.8 | 1.2 |
| 111 | 5% Pt/AWC | 4% Phosphotungstic Acid/SiO$_2$ | TMP | 13.6 | 9.4 |
| 112 | 5% Pt/AWC | Deloxan ® | TMP | 11.6 | 0.9 |
| 113 | 5% Pt/AWC | H-Mordenite | TMP | 18.8 | 0.4 |

The invention claimed is:

1. A method of making 2-butanol comprising:
   (a) contacting a reactant comprising dry or wet 2,3-butanediol, optionally in the presence of at least one inert solvent, with hydrogen and a heterogeneous catalyst system that can function both as an acid catalyst and as a hydrogenation catalyst at a temperature between about 75 and about 300 degrees Centigrade and a hydrogen pressure between about 345 kPa and about 20.7 MPa, to produce a reaction product comprising 2-butanol; and
   (b) recovering 2-butanol from the reaction product.

2. The method of claim 1, wherein the reactant is obtained from a 2,3-butanediol-containing fermentation broth.

3. The method of claim 1, wherein the inert solvent is at least one liquid hydrocarbon, at least one liquid aromatic compound, at least one liquid ether, 2-butanol, or combination thereof.

4. The method of claim 3, wherein the inert solvent is at least one $C_5$ to $C_{20}$ straight-chain, branched or cyclic liquid hydrocarbon, at least one $C_6$ to $C_{20}$ liquid aromatic compound, at least one liquid dialkyl ether wherein the individual alkyl groups of the dialkyl ether are straight-chain or branched, and wherein the total number of carbons of the dialkyl ether is from 4 to 16.

5. The method of claim 4, wherein the individual alkyl groups of the dialkyl ether have from 2 to 5 carbons.

6. The process of claim 1, wherein the heterogeneous catalyst system is comprised of at least one solid acid catalyst and at least one solid hydrogenation catalyst.

7. The process of claim 1, wherein the heterogeneous catalyst system comprises a dual function catalyst.

8. The process of claim 6, wherein the heterogeneous catalyst system comprises at least one solid acid catalyst, and wherein said at least one acid catalyst is selected from the group consisting of (1) heterogeneous heteropolyacids and their salts, (2) natural clay minerals, (3) cation exchange resins, (4) metal oxides, (5) mixed metal oxides, (6) metal salts, and (7) combinations of groups 1 to 6.

9. The process of claim 8, wherein the metal components of groups 4 through 6 are selected from the group consisting of aluminum, chromium, tin, titanium, zirconium, and elements from Groups I, IIa, IIIa, VIIa, VIIIa, Ib and IIb of the Periodic Table of the Elements.

10. The process of claim 8, wherein the acid heterogeneous catalyst system comprises at least one solid acid catalyst, and wherein said at least one solid acid catalyst is selected from the group consisting of cation exchange resins and natural clay minerals.

11. The process of claim 6, wherein the at least one solid acid catalyst is supported on at least one catalyst support.

12. The process of claim 11, wherein the at least one solid acid catalyst is supported, and wherein the at least one solid acid catalyst is present at from about 0.1% to about 20% by weight relative to the catalyst weight plus the support weight.

13. The process of claim 11, wherein the at least one catalyst support is selected from the group consisting of oxides of silica, alumina, titania, compounds thereof or combinations thereof; barium sulfate; calcium carbonate; zirconia; carbons; and combinations thereof.

14. The process of claim 6, wherein the heterogeneous catalyst system comprises at least one solid hydrogenation catalyst, and wherein said at least one solid hydrogenation catalyst comprises a metal selected from the group consisting of nickel, copper, chromium, cobalt, rhodium, ruthenium, rhenium, osmium, iridium, platinum, palladium, platinum black; compounds thereof; and combinations thereof.

15. The process of claim 14, wherein the at least one solid hydrogenation catalyst is selected from the group consisting of ruthenium, iridium, palladium, compounds thereof; and combinations thereof.

16. The process of claim 14, wherein the at least one solid hydrogenation catalyst is supported on at least one catalyst support.

17. The process of claim 16, wherein the at least one solid hydrogenation catalyst is supported, and wherein the at least one solid hydrogenation catalyst is present at from about 0.1% to about 20% by weight relative to the catalyst weight plus the support weight.

18. The process of claim 16, wherein the at least one catalyst support is selected from the group consisting of oxides of silica, alumina, titania; compounds thereof or combinations thereof; barium sulfate; calcium carbonate; zirconia; carbons; and combinations thereof.

19. The process of claim 18, wherein the at least one solid hydrogenation catalyst supported on at least one catalyst support is selected from the group consisting of ruthenium on carbon, ruthenium on alumina, and iridium on carbon.

20. The process of claim 1, wherein the heterogeneous catalyst system comprises:
   (a) at least one unsupported or supported solid acid catalyst wherein the solid acid catalyst is selected from the group consisting of (1) heterogeneous heteropolyacids and their salts, (2) natural clay minerals, (3) cation exchange resins, (4) metal oxides, (5) mixed metal oxides, (6) metal salts and (7) combinations of groups 1 to 6; and
   (b) at least one unsupported or supported hydrogenation catalyst wherein the hydrogenation catalyst is selected from metals from the group consisting of nickel, copper, chromium, cobalt, rhodium, ruthenium, rhenium, osmium, iridium, platinum, palladium, platinum black; compounds thereof; and combinations thereof.

* * * * *